United States Patent
Xu et al.

(10) Patent No.: US 10,722,248 B2
(45) Date of Patent: Jul. 28, 2020

(54) DEPTH MEASUREMENT DEVICE AND GRINDING DEVICE

(71) Applicant: Tinavi Medical Technologies Co., Ltd., Haidian District, Beijing (CN)

(72) Inventors: Jincai Xu, Beijing (CN); Yongqiang Zhao, Beijing (CN)

(73) Assignee: TINAVI MEDICAL TECHNOLOGIES CO., LTD., Beijing (CN)

( * ) Notice: Subject to any disclaimer, the term of this patent is extended or adjusted under 35 U.S.C. 154(b) by 0 days.

(21) Appl. No.: 16/560,264

(22) Filed: Sep. 4, 2019

(65) Prior Publication Data

US 2020/0178985 A1 Jun. 11, 2020

(30) Foreign Application Priority Data

Dec. 7, 2018 (CN) .......................... 2018 1 1497740

(51) Int. Cl.
*A61B 17/16* (2006.01)
*A61B 17/17* (2006.01)
*A61B 90/00* (2016.01)

(52) U.S. Cl.
CPC .......... *A61B 17/1626* (2013.01); *A61B 17/17* (2013.01); *A61B 90/06* (2016.02); *A61B 2090/062* (2016.02)

(58) Field of Classification Search
CPC .......... A61B 17/1666; A61B 2090/062; A61B 17/1746; A61B 34/20; A61B 17/16; A61B 17/17
See application file for complete search history.

(56) References Cited

U.S. PATENT DOCUMENTS

| | | | | |
|---|---|---|---|---|
| 5,037,424 A * | 8/1991 | Aboczsky | ............. | A61F 2/4609 606/91 |
| 5,320,625 A * | 6/1994 | Bertin | ...................... | A61B 5/22 606/91 |
| 6,021,343 A * | 2/2000 | Foley | ..................... | A61B 17/16 600/417 |
| 6,283,971 B1* | 9/2001 | Temeles | ............. | A61B 17/1666 606/79 |
| 7,877,890 B2* | 2/2011 | Weber | .................... | A61B 90/36 33/613 |
| 8,588,892 B2* | 11/2013 | Hladio | .................. | A61F 2/4609 600/431 |

(Continued)

*Primary Examiner* — David W Bates
(74) *Attorney, Agent, or Firm* — Panitch Schwarze Belisario & Nadel LLP (57) ABSTRACT

A depth measurement device includes a guide, a sliding part, a central column and a limit assembly, wherein the guide has a tubular structure. The sliding part is slidably connected to the guide, has a sliding direction parallel to an axial direction of the guide, and is used for connecting a tracer. The central column penetrates through the tubular structure, is able to move in the axial direction and to rotate around an axis, has one tail end for connecting with a cutting tool and another tail end for connecting with a power input. The limit assembly is fixed to the central column, is located on a side of the sliding part adjacent to the other tail end of the central column, and is able to drive the sliding part to synchronously move when moving along with the central column. A grinding device includes the depth measurement device.

12 Claims, 5 Drawing Sheets

(56) References Cited

U.S. PATENT DOCUMENTS

| | | | |
|---|---|---|---|
| 8,961,500 B2* | 2/2015 | Dicorleto | A61B 17/1622 |
| | | | 606/1 |
| 9,161,799 B2* | 10/2015 | Benson | A61B 17/1655 |
| 9,248,002 B2* | 2/2016 | McCarthy | A61B 34/10 |
| 9,393,039 B2* | 7/2016 | Lechner | A61B 17/32070 |
| 9,451,999 B2* | 9/2016 | Simpson | A61B 5/06 |
| 2004/0153080 A1* | 8/2004 | Dong | A61B 17/1666 |
| | | | 606/80 |
| 2004/0171929 A1* | 9/2004 | Leitner | A61B 17/1666 |
| | | | 600/424 |
| 2005/0159751 A1* | 7/2005 | Berthusen | A61B 17/1624 |
| | | | 606/80 |
| 2005/0182320 A1* | 8/2005 | Stifter | A61B 5/103 |
| | | | 600/429 |
| 2008/0255584 A1* | 10/2008 | Beverland | A61B 5/103 |
| | | | 606/130 |
| 2011/0313281 A1* | 12/2011 | Grinberg | A61B 17/16 |
| | | | 600/424 |
| 2012/0157887 A1* | 6/2012 | Fanson | A61F 2/46 |
| | | | 600/595 |
| 2013/0060278 A1* | 3/2013 | Bozung | A61B 17/1703 |
| | | | 606/205 |
| 2015/0190151 A1* | 7/2015 | Budhabhatti | A61B 17/1666 |
| | | | 606/96 |
| 2015/0272696 A1* | 10/2015 | Fry | A61F 2/4609 |
| | | | 606/87 |
| 2017/0196506 A1* | 7/2017 | Behzadi | A61B 7/023 |
| 2017/0196704 A1* | 7/2017 | Behzadi | A61F 2/4609 |
| 2017/0196705 A1* | 7/2017 | Behzadi | A61F 2/4603 |

* cited by examiner

DEPTH MEASUREMENT DEVICE AND GRINDING DEVICE

CROSS-REFERENCE TO RELATED APPLICATION

This application claims priority under 35 U.S.C. § 119(b) to Chinese Application No. 201811497740.5, filed Dec. 7, 2018, the disclosure of which is incorporated herein by reference in its entirety.

BACKGROUND OF THE INVENTION

1. Technical Field

The invention relates to the field of medical instruments, in particular to a depth measurement device and a grinding device.

2. Description of Related Art

During orthopedic surgery, bones usually need to be drilled or ground, and in this operation process, the drilling or grinding depth needs to be controlled. The traditional depth measurement devices measure the depth through a graduated scale, and then calculate the feed depth according to the value difference of the scale before and after depth measurement.

Due to the large errors of a method for measuring the feed depth in the prior art, a depth measurement device having higher accuracy is expected to be invented.

BRIEF SUMMARY OF THE INVENTION

The invention provides a depth measurement device and a grinding device which can improve the depth test accuracy.

On the one hand, the invention provides the depth measurement device which includes a guide, a slicing part, a central column and a limit assembly, wherein the guide is in a tubular structure; the sliding part is slidably connected to the guide, has a sliding direction parallel to an axial direction of the guide, and is used for connecting with a tracer; the central column penetrates through the tubular structure, is able to move in the axial direction and to rotate around an axis, and has one tail end for connecting with a cutting tool and another tail end for connecting with a power input; and the limit assembly is fixed to the central column, is located on a side of the sliding part adjacent to the other tail end of the central column, and is able to drive the sliding part to synchronously move when moving along with the central column.

In one embodiment of the invention, a passage is arranged in the sliding part and is matched with the outer surface of the guide, and the guide penetrates through the passage, so that the sliding part can slide relative to the guide.

In one embodiment of the invention, one of the outer surface of the guide and the inner surface, facing the passage, of the sliding part is provided with a groove, and the other is provided with a protrusion slidably matched with the groove; and an extension direction of the groove is parallel to an axial direction of the central column.

In one embodiment of the invention, the depth measurement device further includes an elastic part, wherein the elastic part is arranged between the sliding part and the guide and is used for providing damping when the sliding part moves towards one tail end of the central column.

In one embodiment of the invention, the elastic part is a spring and is coaxially arranged in the passage.

In one embodiment of the invention, the sliding part is fixed to an axial position of the central column, so that the sliding part and the central column can synchronously move in the axial direction of the central column.

In one embodiment of the invention, the limit assembly includes a clamping device clamped on the central column.

In one embodiment of the invention, the limit assembly further includes a limit block, wherein the limit block is arranged around the central column and is located on a side, facing the sliding part, of the clamping device.

In one embodiment of the invention, the depth measurement device further includes the tracer, wherein the tracer is connected to the sliding part and includes three or more markers, and at least one marker is not collinear with the other markers.

In one embodiment of the invention, the markers are reflection balls or light-emitting diodes.

In one embodiment of the invention, the side wall of the guide is connected with a connection handle, and the side wall of the sliding part is connected with a handle.

On the other hand, the invention provides a grinding device which includes the depth measurement device in any one of the embodiments mentioned above.

According to the depth measurement device of the invention, the limit assembly abuts against the sliding part, so that the central column can synchronously move along with the sliding part; and the feed depth of the central column can be detected through detection of the displacement of the sliding part, so that the feed amount of the central column can be detected.

In some embodiments, the sliding part is firstly moved by a preset distance in an initial state (the limit assembly abuts against the sliding part), and then the central column is fed; and when the limit assembly on the central column abuts against the sliding part again, feeding of the central column by the preset distance is completed. In this way, the controllability of the feed amount of the central column is improved, and the instability caused by manual feeding is avoided. The grinding device including the depth measurement device of the invention can avoid excessive grinding.

BRIEF DESCRIPTION OF THE SEVERAL VIEWS OF THE DRAWINGS

Those skilled in the art can appreciate other characteristics, objectives, and advantages of the invention by reading the following detailed description of non-restrictive embodiments with reference to the following accompanying drawings, wherein identical or similar reference signs in the drawings represent identical or similar characteristics.

DETAILED DESCRIPTION OF THE INVENTION

The characteristics and illustrative embodiments of the invention are detailed below. For a better understanding of the objectives, technical solutions, and advantages of the invention, the invention is further expounded below with reference to the accompanying drawings and embodiments. It should be understood that the embodiments in the following description are only used to explain the invention, and are not intended to limit the invention. Those skilled in the art can implement the invention without some of these specific details. These illustrative embodiments in the following description are used to fulfill a better apprehension of the invention.

What should be pointed out is that the relational terms such as "first" and "second" in this description are only used to distinguish one entity or operation from the other, and do not mean or indicate that these entities or operations have any actual relationships or are configured in any actual sequences. In addition, the terms such as "comprise", "include" or any other variations refer to non-exclusive inclusion which means that a process, method, article, or device including a series of elements not only includes these elements listed, but also includes other elements that are not explicitly listed, or further includes inherent elements of this process, method, article, or device. Unless otherwise specifically limited, the process, method, article, or device referred to not only includes the elements defined by the term "include", but also may include other similar elements.

It should be apprehended that the statement, used for describing the structure of a component, that one layer or area is located "on" or "above" the other one may indicate that one layer or area is directly located on the other one, or indicate that other layers or areas exist between these two layers or areas. Moreover, if this component is turned upside down, this layer or area will be located "under" or "below" the other one.

Figure 1:
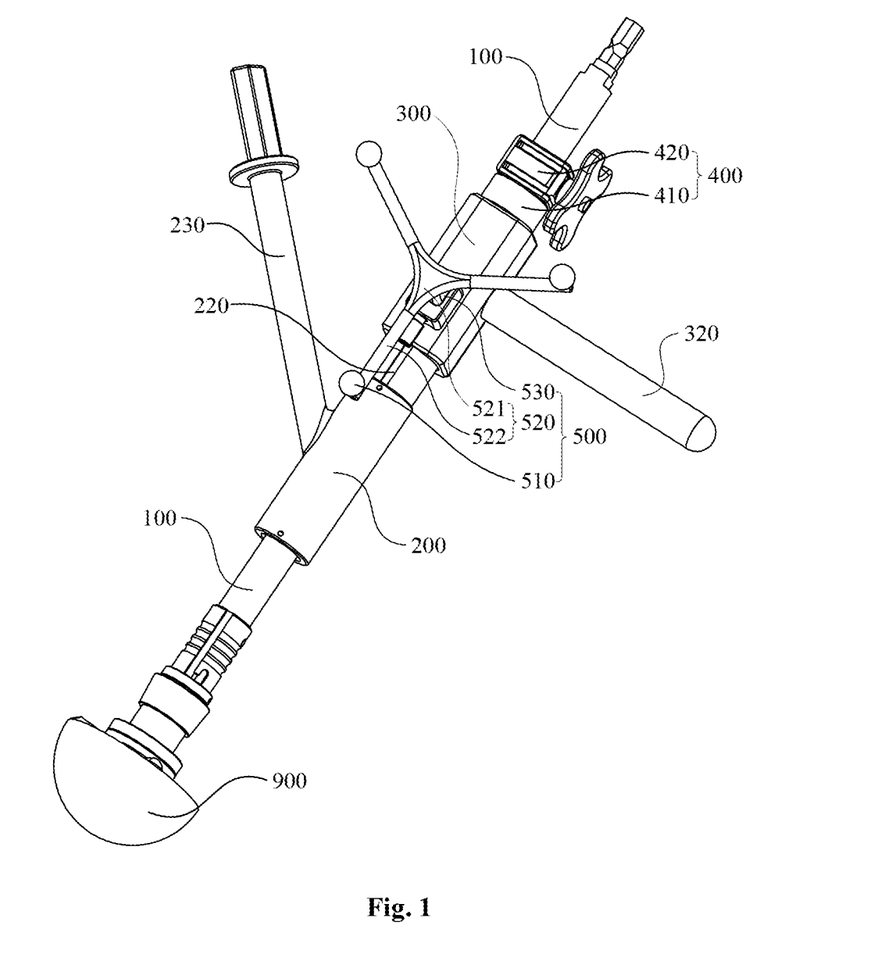
FIG. 1 is a perspective view of a depth measurement device of the invention.
Figure 2:
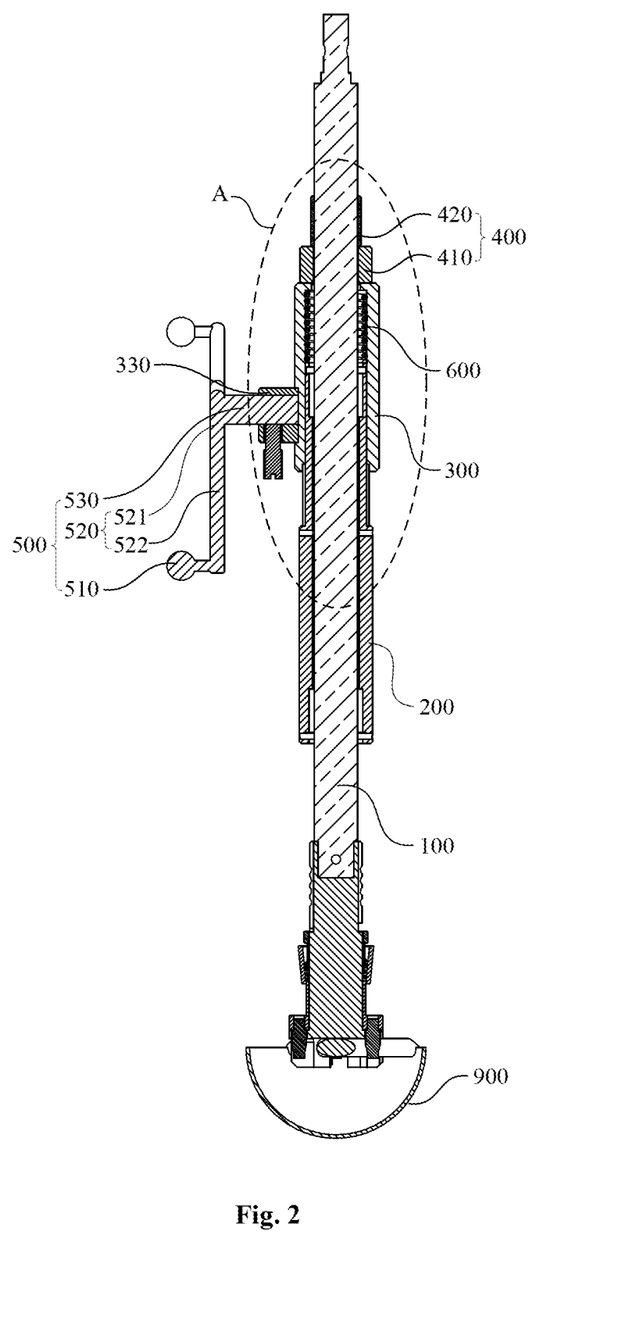
FIG. 2 is a sectional view of the depth measurement device of the invention.
Figure 3:
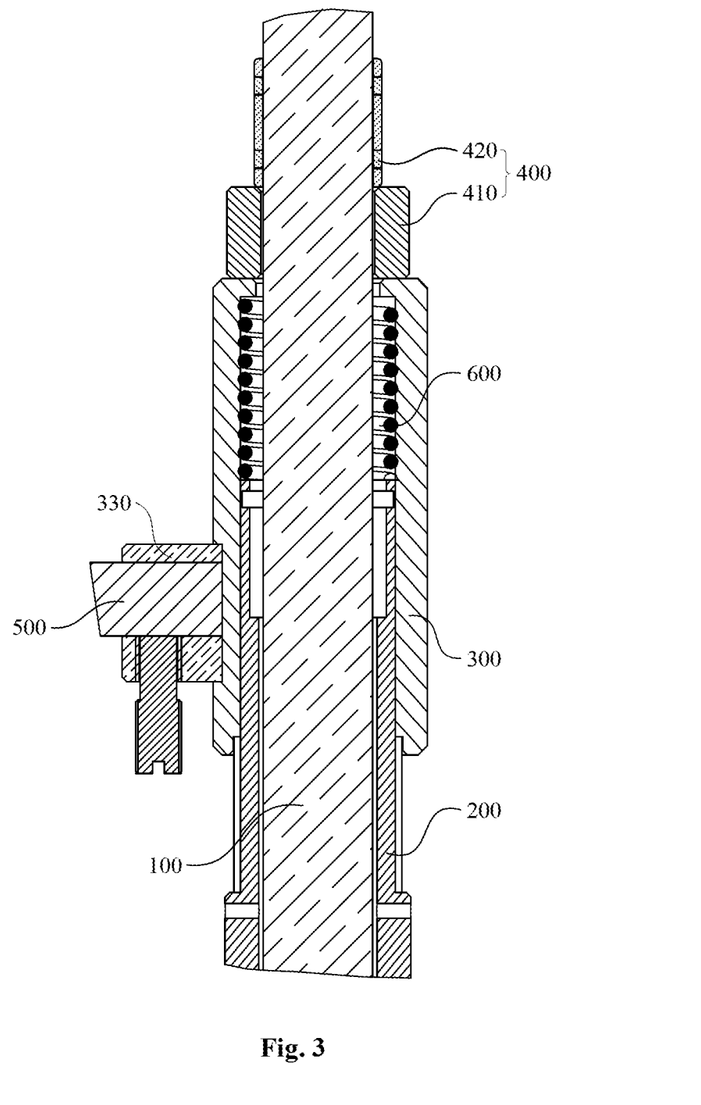
FIG. 3 is a partial enlarged view of area A in FIG. 2.

FIG. 1 and FIG. 2 are respectively a perspective view and a sectional view of a depth measurement device of the invention, and FIG. 3 is a partial enlarged view of area A in FIG. 2. The depth measurement device in this embodiment includes a central column 100, a guide 200, a sliding part 300 and a limit assembly 400.

The depth measurement device in this embodiment can be connected with other parts to form functional devices, which have various purposes and can detect feed depths. For instance, the central column 100 includes a front end and a rear end opposite to the front end, wherein the front end can be connected with a grinding tool such as a saw file, and the rear end can be connected with a rotational output device such as a hand drill or an electric drill. The rotational output device drives the central column 100 to rotate around a central axis so as to drive the grinding tool to rotate to grind or drill an object to be ground; and meanwhile, the central column 100 can move in an axial direction, for instance, the central column 100 is fed towards the object to be ground. The depth measurement device in this embodiment can detect the movement distance or the feed depth of the central column 100 in the axial direction.

The terms "front end" and "rear end" in this description are only used for expressing two opposite ends, which can be randomly exchanged, of a component.

In one embodiment of the invention, the guide 200 is in a tubular structure; the sliding part 300 is slidably connected to the guide 200, has a sliding direction parallel to an axial direction of the guide 200, and is connected with a tracer; and the central column 100 penetrates through the tubular structure, is able to move in the axial direction and to rotate around an axis, and has two tail ends, wherein one tail end of the central column 100 is connected with a cutting tool, and the other tail end of the central column 100 is connected with a power input. In this embodiment, one tail end of the central column 100 is a front tail end, and the other tail end of the central column 100 is a rear tail end.

The limit assembly 400 is fixed to the central column 100, is located on a side, adjacent to the other tail end of the central column 100, of the sliding part 300, and drives the sliding part 300 to synchronously move when rotating along with the central column 100.

According to the depth measurement device in this embodiment, the limit assembly 400 drives the sliding part 300 to synchronously move when moving along with the central column 100, and the sliding part 300 does not rotate along with the central column, so that the tracer 500 can be arranged on the sliding part 300, a matched optical camera detects the displacement of the sliding part 300 by recognizing the movement of the tracer 500, so as to detect the feed depth of the central column 100, and accordingly, the feed amount of the central column 100 is detected and displayed.

In some embodiments, the sliding part 300 is firstly moved by a preset distance in an initial state (the limit assembly 400 abuts against the sliding part 300), and then the central column 100 is fed; and when the limit assembly 400 on the central column 100 abuts against the sliding part 300 again, feeding of the central column 100 by the preset distance is completed. In this way, the controllability of the feed amount of the central column 100 is improved, and the instability caused by manual feeding is avoided. The grinding device including the depth measurement device in this embodiment can avoid excessive grinding.

Figure 4:
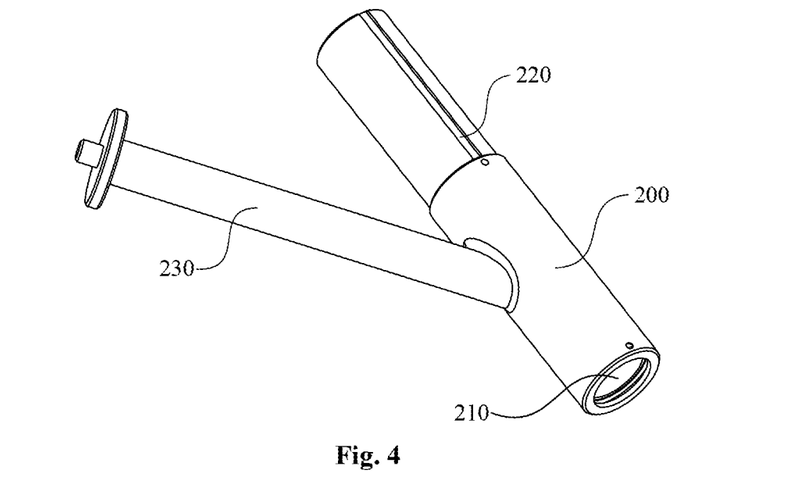
FIG. 4 is a perspective view of a guide of the invention.
Figure 5:
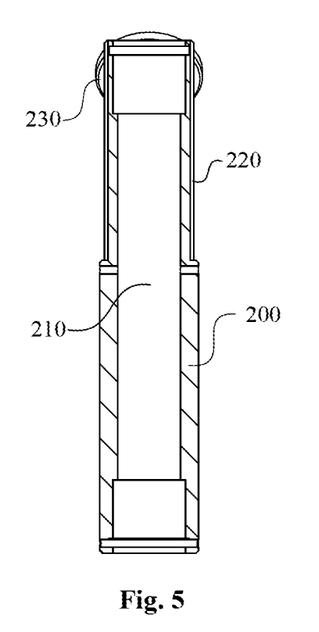
FIG. 5 is a sectional view of the guide of the invention.

FIG. 4 and FIG. 5 are respectively a perspective view and a sectional view of the guide of the invention. In this embodiment, an axially-extending first passage 210 is arranged in the guide 200 in the tubular structure, and has an inner surface matched with the outer surface of the central column 100, and the central column 100 penetrates through the first passage 210 and can slide in the extension direction of the first passage 210. In some embodiments, the central column 100 can rotate in the first passage 210 around the central axis of its own.

Figure 6:
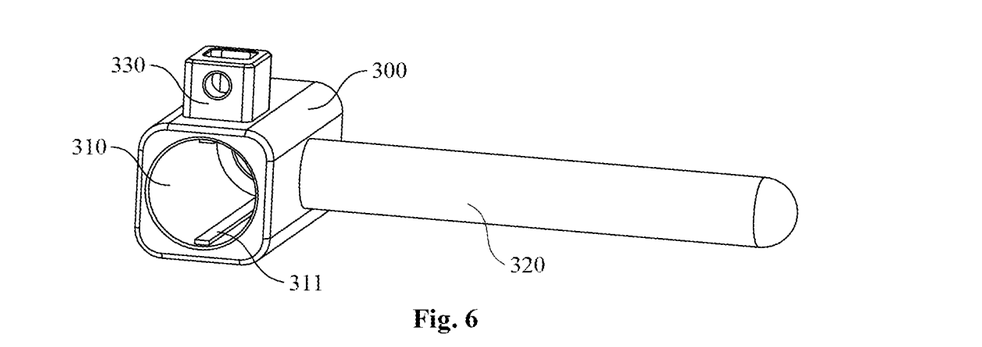
FIG. 6 is a perspective view of a sliding part of the invention.
Figure 7:
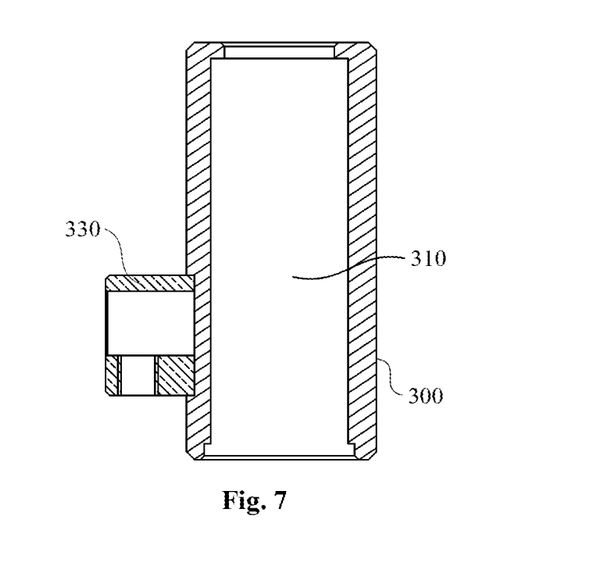
FIG. 7 is a sectional view of the sliding part of the invention.

FIG. 6 and FIG. 7 are respectively a perspective view and a sectional view of the sliding part of the invention. The sliding part 300 is slidably connected to the guide 200 and has a sliding direction parallel to the axial direction of the guide 200. In this embodiment, the sliding part 300 is hollow and columnar, a second passage 310 is arranged in the sliding part 300 and is matched with the outer surface of the guide 200, and the guide 200 penetrates through the second passage 310, so that the sliding part 300 can slide relative to the guide 200; the outer surface of the sliding part 300 is approximately prismatic, and the second passage 310 is approximately cylindrical; and in other embodiments, the outer surface of the sliding part 300 may be in other shapes, and the second passage 310 can be correspondingly adjusted according to shape changes of the outer surface of the guide 200. For instance, when the outer surface of the guide 200 is prismatic, the second passage 310 is a prismatic passage matched with the prismatic outer surface of the guide 200. Understandably, in some embodiments, the sliding part 300 can be in sliding fit with the guide 200 through other structures such as a slide rail instead of the second passage 310, so as to slide relative to the guide 200.

In this embodiment, the outer surface of the guide 200 is provided with a groove 220, the inner surface, facing the second passage 310, of the sliding part 300 is provided with a protrusion 311 matched with the groove 220, and the extension direction of the groove 220 is parallel to the axial direction of the guide 200. Or, in other embodiments, the inner surface, facing the second passage 310, of the sliding part 300 is provided with the groove, the outer surface of the guide 200 is provided with the protrusion matched with the groove, and the extension direction of the groove is parallel to the axial direction of the guide 200. Through the configuration of the groove axially parallel to the guide 200 and the protrusion slidably matched with the groove, the sliding part 300 and the guide 200 can synchronously rotate around a central axis parallel to the axial direction of the guide 200.

In some embodiments, a connection handle 230 is connected to the side wall of the guide 200, and is used for connecting the guide 200 to a mechanical arm, so that the mechanical arm can drive the depth measurement device to move. In some embodiments, a handle 320 is connected to the side wall of the sliding part 300, and can be held or be fixedly connected to other devices to prevent the sliding part 300 against unnecessary rotation during the movement of the central column 100. Furthermore, in this embodiment, the groove 220 and the protrusion 311 matched with the groove 220 are arranged between the guide 200 and the sliding part 300, so that the guide 200 is further prevented against unnecessary rotation.

Referring to FIG. 2 and FIG. 3, the depth measurement device in this embodiment further includes an elastic part 600, wherein the elastic part 600 is arranged between the sliding part 300 and the guide 200 and is used for providing damping when the sliding part 300 moves towards one tail end of the central column 100.

In this embodiment, the guide 200 and the sliding part 300 each have a front end and a rear end opposite to the front end, wherein the front end of the guide 200 and the front end of the sliding part 300 face the front end of the central column 100, and the rear end of the guide 200 and the rear end of the 300 face the rear end of the central column 100; and the rear end of the sliding part 300 can extend out of the rear end of the guide 200 by a preset distance, and moves close to or away from the rear end of the guide 200 when the sliding part 300 slides relative to the guide 200.

The elastic part 600 may be a spring and is coaxially arranged in the second passage 310. The rear end of the sliding part 300 is provided with an abutting part extending towards the central axis; one end of the spring is connected to the abutting part at the rear end of the sliding part 300, and the other end of the spring is connected to the rear end of the guide 200; and the sliding part 300 is ejected to the limit assembly 400 by the spring so as to abut against the limit assembly 400.

The elastic part 600 is configured to increase damping among the sliding part 300, the guide 200, the limit assembly 400, and the central column 100 connected with a locking piece so as to form buffering, and accordingly, the frictional force between the central column 100 and the guide 200 is prevented from too small, which nay otherwise cause impact to the guide 200. Understandably, the elastic part 600 is not an essential structure and can be omitted in other embodiments; and furthermore, if the elastic part 600 is configured, the elastic part 600 is not limited to the spring and is configured in other forms such as an elastic slice.

In some embodiments, the sliding part 300 is provided with the locking piece which is used for locking the sliding part 300 and the central column 100 and/or locking the sliding part 300 and the guide 200; when the locking piece is used for locking the sliding part 300 and the central column 100, the sliding part 300 and the central column 100 which are locked together synchronously move, and the tracer connected with the sliding part 300 simultaneously displays the displacement of the central column 100; and when the locking piece is used for locking the sliding part 300 and the guide 200, the sliding part 300 is locked at a preset position, such as a position at a preset feed distance from an initial position, in the axial direction of the guide 200.

In this embodiment of the invention, the sliding part 300 and the central column 100 are not directly connected, and synchronously move in the axial direction when the limit assembly 400 abuts against the sliding part 300; or, the sliding part 300 independently moves in the axial direction, so that non-synchronous movement is fulfilled.

In other embodiments, the sliding part 300 is fixed to an axial position of the central column 100, so that the sliding part 300 and the central column 100 can synchronously move in the axial direction of the central column 100. Moreover, whether or not the central column 100 can rotate relative to the sliding part 300 around the central axis of its own can be set according to practical requirements. In some embodiments, the central column 100 and the sliding part 300 synchronously move in the axial direction of the central column 100, but the central column 100 can still rotate relative to the sliding part 300 around the central axis.

Referring to FIG. 1 to FIG. 3, the limit assembly 400 is arranged on the central column 100 to limit the sliding part 300, In this embodiment, the central column 100 is exposed out of the front end and the rear end of the guide 200, the limit assembly 400 is arranged between the rear end (the other tail end) of the central column 100 and the rear end of the guide 200, and the sliding part 300 is slidably arranged at the rear end of the guide 200.

In this embodiment, the limit assembly 400 includes a limit block 410 and a clamping device 420, wherein the clamping device 420 is clamped on the central column 100; and the limit block 410 is arranged around the central column 100, and is located on a side, facing the sliding part 300, of the clamping device 420, that is to say, the clamping device 420 is located on a side, away from the sliding part 300, of the limit block 410, so that the limit block 410 is limited at a preset position. After the limit block 410 is limited at the preset position by the clamping device 420, the sliding part 300 slides to abut against the limit block 410. Specifically, the rear end of the sliding part 300 abuts against the limit block 410.

In the case where the sliding part 300 is connected with the tracer, the depth measurement device further includes the tracer 500 connected with the sliding part 300. The tracer 500 synchronously moves along with the sliding part 300 to mark the feed depth of the central column 100, and can more accurately and visually display the feed amount of the central column 100 in cooperation with an optical detection instrument matched with the tracer 500.

For instance, the tracer 500 in this embodiment is an optical tracer which can be recognized by an optical navigation camera, and the position of tracer 500 is recorded in real time and can accurately displayed on a display by means of programing so that the accuracy of the depth measurement device is greatly improved.

The tracer 500 includes three or more markers 510, wherein at least one marker 510 is not collinear with the other markers 510, In this embodiment, the tracer 500 includes three markers 510 which are distributed in a regular triangle shape. The markers 510 are passive reflection balls or active light-emitting diodes.

In this embodiment, the tracer 500 further includes a support 520 and a support connector 530, wherein the support 520 includes a center part 521 and three or more connection parts 522 extending outwards from the center part 521, and the markers 510 are arranged on the connection parts 522. The three or more connection parts 522 are arranged in the same plane, and the support connector 530 is fixed to the center part 521 of the support 520, is perpendicular to the plane in an axial direction, and connects the support 520 with the sliding part 300.

In some embodiments, an installation rack 330 is arranged on the side wall of the sliding part 300 and is used for mounting the tracer 500; and an installation hole marched with the support connector 530 and a pin hole connected to the inner wall of the installation hole are formed in the installation rack 330, the support connector 530 is arranged in the installation hole, and a fixed pin penetrates through the pin hole to be fixed to the support connector 530, so that the tracer 500 is connected to the sliding part 300, the markers 510 of the tracer 500 stably and synchronously move along with the sliding part 300, and the displacement track of the sliding part can be recorded in real time.

The invention further provides a grinding device. As shown in FIG. 1 and FIG. 2, the grinding device includes, for instance, the depth measurement device of the above embodiment, and a grinding tool 900, wherein the grinding tool 900 is connected to one tail end of the central column 100. In this embodiment, the grinding tool 900 is a saw file connected to the front end of the central column 100, and the rear end of the central column 100 is connected to a rotational output device such as a hand drill or an electric drill; and the rotational output device drives the central column 100 to rotate around the central axis so as to drive the grinding tool 900 to rotate to grind or drill an object to be ground; and meanwhile, and the central column 100 can move in the axial direction, for instance, the central column 100 is fed towards the object to be ground. The grinding device of the invention can detect the movement distance or the feed depth of the grinding tool 900 in the axial direction of the central column 100 while grinding or drilling the object to be ground.

According to the grinding device of the invention, the limit assembly 400 abuts against the sliding part 300, so that the central column 100 synchronously moves along with the sliding part 300; and the feed depth of the central column 100 can be detected through detection of the displacement of the sliding part 300, and the feed amount of the central column can be detected and displayed.

In some embodiments, the sliding part 300 is firstly moved by a preset distance in an initial state (the limit assembly 400 abuts against the sliding part 300), and then the central column 100 is fed; and when the limit assembly 400 on the central column 100 abuts against the sliding part 300 again, feeding of the central column 100 and the grinding tool 900 by the preset distance is completed. In this way, the controllability of the feed amounts of the central column 100 and the grinding tool 900 is improved, and the instability caused by hand feed is avoided, and accordingly, excessive grinding is avoided.

The embodiments mentioned above do not illustrate all details of the invention and should not be regarded as all possible ones of the invention. Clearly, various modifications and variations can be made with reference to the above description. These embodiments specifically described in this description are used to better explain the principle and actual application of the invention, so that those skilled in the art can easily implement the invention and make modifications based on the invention. The invention is limited by the claims, and their full scope and equivalents.

What is claimed is:

1. A depth measurement device for measuring a feed depth of a surgery tool in a surgery, the device comprising:
    a guide, having a tubular body;
    a sliding part, sliding on an outer surface of the tubular body, having a sliding direction parallel to an axial direction of the tubular body, and connecting with a tracer;
    a central column, passing through the tubular body along the axial direction, being able to move in the axial direction and rotate around a central axis of the central column, and having one tail end for connecting with the surgery tool and another tail end for connecting with a power input; and
    a limit assembly, being used to limit a position of the sliding part, fixing to the central column, being closer to said another tail end of the central column, and being able to drive the sliding part to synchronously move when moving along with the central column;
    wherein a displacement of the sliding part can be detected by recognizing movement of the tracer, so as to obtain the feed depth of the surgery tool.

2. The depth measurement device of claim 1, wherein a passage is arranged in the sliding part and is matched with an outer surface of the guide, and the guide penetrates through the passage, so that the sliding part can slide relative to the guide.

3. The depth measurement device of claim 2, wherein one of the outer surface of the guide and an inner surface, facing the passage, of the sliding part is provided with a groove, and the other is provided with a protrusion slidably matched with the groove; and an extension direction of the groove is parallel to an axial direction of the central column.

4. The depth measurement device of claim 2, further comprising:
    an elastic part, arranging between the sliding part and the guide and being used for providing damping when the sliding part moves towards the one tail end of the central column.

5. The depth measurement device of claim 4, wherein the elastic part is a spring and is coaxially arranged in the passage.

6. The depth measurement device of claim 1, wherein the sliding part is fixed to an axial position of the central column, so that the sliding part and the central column can synchronously move in the axial direction of the central column.

7. The depth measurement device of claim 1, wherein the limit assembly comprises:
    a clamping device, clamping on the central column.

8. The depth measurement device of claim 1, wherein the limit assembly comprises:
    a limit block, arranging around the central column and locating on a side, facing the sliding part, of a clamping device.

9. The depth measurement device of claim 1, further comprising:
    a tracer, connecting to the sliding part and comprising three or more markers, wherein at least one of the markers is not collinear with the other markers.

10. The depth measurement device of claim 9, wherein the markers are reflection balls or light-emitting diodes.

11. The depth measurement device of claim 1, wherein a side wall of the guide is connected with a connection handle; and
    a side wall of the sliding part is connected with a handle.

12. A grinding device, comprising:
the depth measurement device of claim 1; and
a surgery tool, connecting to the one tail end of the central column.

\* \* \* \* \*